United States Patent
Mazur et al.

(10) Patent No.: US 9,427,393 B2
(45) Date of Patent: Aug. 30, 2016

(54) DISPERSIONS CONTAINING ENCAPSULATED MATERIALS AND COMPOSITIONS USING SAME

(71) Applicant: NuSil Technology LLC, Carpinteria, CA (US)

(72) Inventors: Angelique Mazur, Mougins (FR); Claire Prudhon, Mougins (FR); Michel Bassens, Mougins (FR); Mathieu Goutayer, Marseilles (FR); Sebastein Bardon, Marseilles (FR)

( * ) Notice: Subject to any disclaimer, the term of this patent is extended or adjusted under 35 U.S.C. 154(b) by 0 days.

(21) Appl. No.: 14/672,063

(22) Filed: Mar. 27, 2015

(65) Prior Publication Data

US 2015/0272861 A1   Oct. 1, 2015

Related U.S. Application Data

(60) Provisional application No. 61/971,982, filed on Mar. 28, 2014.

(51) Int. Cl.
| | |
|---|---|
| *A61K 8/11* | (2006.01) |
| *A61K 8/34* | (2006.01) |
| *A61K 8/898* | (2006.01) |
| *A61Q 17/04* | (2006.01) |
| *A61K 8/81* | (2006.01) |

(52) U.S. Cl.
CPC ............... *A61K 8/898* (2013.01); *A61K 8/11* (2013.01); *A61K 8/345* (2013.01); *A61K 8/8147* (2013.01); *A61Q 17/04* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,540,927 A | 7/1996 | Jason et al. | |
| 5,637,306 A | 6/1997 | Cauwet et al. | |
| 6,113,931 A * | 9/2000 | Bonda | A61K 8/35 424/400 |
| 6,818,296 B1 * | 11/2004 | Garces Garces | A61K 8/0208 264/4.1 |
| 2005/0175651 A1 | 8/2005 | Simonnet et al. | |
| 2006/0141046 A1 | 6/2006 | Cattaneo | |
| 2007/0243147 A1 * | 10/2007 | Wolber | A61K 8/671 424/59 |
| 2014/0045949 A1 | 2/2014 | Goutayer et al. | |

FOREIGN PATENT DOCUMENTS

| | | |
|---|---|---|
| EP | 1808479 A1 | 7/2007 |
| WO | 2012120043 A2 | 9/2012 |
| WO | WO2012120043 * | 9/2012 |
| WO | 2013113830 A1 | 8/2013 |

OTHER PUBLICATIONS

International Search Report & Written Opinion of the International Searching Authority PCT/US2015/022930 dated Jun. 30, 2015.

* cited by examiner

*Primary Examiner* — Jennifer Berrios
(74) *Attorney, Agent, or Firm* — McDermott Will & Emery LLP

(57) ABSTRACT

Dispersions of an encapsulated material by a polymeric membrane in a medium are disclosed. Such dispersions are useful in topical compositions including cosmetics and sunscreens.

16 Claims, No Drawings

DISPERSIONS CONTAINING ENCAPSULATED MATERIALS AND COMPOSITIONS USING SAME

CROSS-REFERENCE TO RELATED APPLICATION

This application claims the benefit of U.S. Provisional Application No. 61/971,982 filed Mar. 28, 2014 the entire disclosure of which is hereby incorporated by reference herein.

TECHNICAL FIELD

The present disclosure pertains to dispersions of encapsulated material dispersed in a medium that is substantially immiscible with the encapsulated material. Such dispersions include an encapsulated material, e.g. a composition including either polyorganosiloxane or water, dispersed in a medium, e.g., an aqueous medium such as an aqueous gel or in an oil such as a polyorganosiloxane, wherein the encapsulated material and medium are substantially immiscible and the encapsulated material is encapsulated by a polymeric membrane. The dispersions can be included in compositions for use in cosmetic, dermatologic, personal care, health care and household applications.

BACKGROUND

Encapsulation takes many forms with the main objectives of controlled release or delivery of the agent(s) and protection of the agent(s) from degradation prior to the intended delivery. Additionally encapsulations may be used to incorporate agents that may be difficult or impossible to deliver without irritating levels of stabilizers such as emulsifiers or surfactants.

Several references describe encapsulation via coacervation. For example, U.S. Pat. No. 5,540,927 discloses a process for microencapsulation of materials by means of complex coacervation employing gelatin and polyaspartic acid. Polyaspartic acid or a salt thereof is employed to provide a counter ion to the gelatin which, when induced to precipitate from solution by cooling and/or pH change forms a wall around the material. The reference addresses leakage and failure to encapsulate a target solution. WO 2013113830 A1, WO 2012120043A3, and U.S.2014/0045949 describe complex methods for preparing capsules including a liquid core, a stiffened intermediate shell, and an outer gel shell, including a step of forming a multi-component drop, a gelling step, and a stiffening step via an interaction of a coacervate precursor system introduced at the interface of the formation of the droplet to be encapsulated.

Previous techniques, however, suffered some disadvantages such as phase mixing between the encapsulated material and non-encapsulated material, exposure of the encapsulated material to environmental conditions that allowed degradation of the encapsulated material and lengthy steps in the process. In addition, most of the prior techniques only briefly describe topical formulations.

SUMMARY OF THE DISCLOSURE

An advantage of the present disclosure is a dispersion comprising an encapsulated material dispersed in a medium that is substantially immiscible with the encapsulated material. The dispersions of the encapsulated material can exist and can be formed in a substantially immiscible medium without use of a surfactant.

Another advantage of the present disclosure is the use of such dispersions in cosmetic, dermatologic, personal care, health care and household applications These and other advantages are satisfied, at least in part, by a dispersion comprising an encapsulated material, e.g. a composition including either polyorganosiloxane or water, dispersed in a medium, e.g., an aqueous medium such as an aqueous gel or in an oil such as a polyorganosiloxane, wherein the encapsulated material and medium are substantially immiscible and the encapsulated material is encapsulated by a polymeric membrane. Advantageously, the dispersion does not include a surfactant for dispersing the encapsulated material in the medium.

Dispersions of an encapsulated polyorganosiloxane can exist and can be formed in a substantially immiscible medium without use of a surfactant. The dispersions can be formed by interfacial coacervation which forms the polymeric membrane encapsulating the polyorganosiloxane. Similarly, dispersions of an encapsulated aqueous composition can exist and can be formed in a substantially immiscible medium without use of a surfactant.

Embodiments of the present disclosure include wherein the average size of the encapsulated material dispersed in the medium is less than 500 microns, e.g., the average size of the encapsulated material is between 5 microns to 300 microns such as between 10 microns and 100 microns. In other embodiments, the encapsulated polyorganosiloxane can be one or more polyorganosiloxanes composed principally of dimethylsiloxane units (e.g., dimethicone and/or a cross-linked dimethicone), and/or one or more active agents, e.g., a sunscreen agent. In some embodiments, the polymeric membrane encapsulating the polyorganosiloxane can be composed of an anionic polymer, e.g., polyacrylic acid, and a cationic polymer, e.g., an amine functionalized polyorganosiloxane such as an amine functionalized methicone or dimethicone, e.g., amodimethicone.

Another aspect of the present disclosure includes a topical composition, e.g., a cosmetic, sunscreen, etc., comprising any of the above-referenced dispersions.

Embodiments include a topical cosmetic or sunscreen composition that can be applied to the skin and that is translucent or completely transparent to the naked eye wherein the medium is an aqueous medium or gel containing glycerin. In some embodiments, the composition includes a high level of glycerin, e.g. greater than 10 wt % of glycerin in the total formulation. In other embodiments, the composition includes glycerin in an amount of between 15 wt % to 65 wt % of the total composition and without any appreciable sensation of tack due to the glycerin.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention.

DETAILED DESCRIPTION OF THE DISCLOSURE

The present disclosure relates to dispersions comprising an encapsulated material dispersed in a medium that is substantially immiscible with the encapsulated material. In one aspect of the present disclosure, the encapsulated material includes a hydrophobic polyorganosiloxane dispersed in an aqueous medium. The dispersion of the encapsulated polyorganosiloxane can exist and can be formed in the substantially immiscible medium, e.g., an aqueous medium, without use of a surfactant, e.g., without use of detergents, wetting agents, emulsifiers, etc.

The dispersions of the present disclosure can also be of relatively high viscosity, e.g., greater than about 20,000 cP, such as greater than about 30,000, 40,000, 50,000 cP, or higher and used as an ingredient in a topical composition. In one aspect of the present disclosure, the dispersions of the present disclosure and topical compositions including them can be made visually translucent or visually transparent. Visually transparent materials pass light and details of objects behind such materials can be visually observed through the material. In contrast, visually translucent materials pass diffuse light and details of objects behind such materials are visually observed through the material as blurred or obscured. Visually opaque materials do not any significant pass light.

In one aspect of the present disclosure, the average size of the encapsulated polyorganosiloxane can vary but is preferably less than about 500 μm. It is believed that encapsulated material having an average size of less than 500 microns, such as between 5 to 300 μm, e.g., between 10 to 100 μm, facilitates good sensory feel and further reduces light scatter in the visible region thereby improving transparency of the dispersion comprising the encapsulated material and compositions including the dispersion.

In another aspect of the present disclosure, the encapsulated material includes a hydrophilic aqueous composition dispersed in a hydrophobic medium. The dispersion of the aqueous composition can exist and can be formed in the substantially immiscible medium, e.g., a polyorganosiloxane, without use of a surfactant, e.g., without use of detergents, wetting agents, emulsifiers, etc. The dispersions of the present disclosure can also be of relatively high viscosity, e.g., greater than about 20,000 cP, such as greater than about 30,000, 40,000, 50,000 cP, or higher and used as an ingredient in a topical composition. In one aspect of the present disclosure, the dispersions of the present disclosure and topical compositions including them can be made visually translucent or visually transparent. The average size of the encapsulated hydrophilic aqueous composition can vary but is preferably less than about 500 μm, such as between 5 to 300 μm, e.g., between 10 to 100 μm. It is believed such an average size facilitates good sensory feel and transparency.

Polyorganosiloxane suitable for the present disclosure can be in the form of any fluid, gum, wax, resin, elastomer in a liquid, paste or powder form or mixtures thereof. If the polyorganosiloxane has a viscosity greater than 1,000,000 cP, it can be blended with the low viscosity volatile or nonvolatile siloxanes such as hexamethyldisiloxane or other short linear siloxanes and cyclopentasiloxane or other cyclic siloxanes or branched siloxanes or mixtures. Polyorganosiloxanes suitable for the present disclosure include one or more linear or branched polyorganosiloxanes. Preferably the one or more polyorganosiloxanes are composed principally of dimethylsiloxane units with the other units being represented by monomethylsiloxane, trimethylsiloxane, methylvinylsiloxane, methylethylsiloxane, diethylsiloxane, methylphenylsiloxane, diphenylsiloxane, ethylphenylsiloxane, vinylethylsiloxane, phenylvinylsiloxane, 3,3,3-trifluoropropylmethylsiloxane, dimethyldiphenylsiloxane, dimethylphenylsiloxane, methylphenylvinylsiloxane, dimethylethylsiloxane, 3,3,3-trifluoropropylmethyldimethylsiloxane, mono-3,3,3-trifluoropropylsiloxane, polyethyleneglycol and/or polypropyleneglycol methylsiloxanes, polyethyleneglycol and/or polypropyleneglycol phenylsiloxanes, polyethyleneglycol and/or polypropyleneglycol alkylsiloxanes polyethyleneglycol and/or polypropyleneglycol 3,3,3-trifluoropropylmethylsiloxanes, $C_3$-$C_{60}$ alkyl methylsiloxanes, $C_3$-$C_{60}$ alkylphenylsiloxanes, aminoalkylsiloxane, diaminoalkylsiloxane, monophenylsiloxane, monovinylsiloxane and other combinations. Medical grade and medical quality ultrapure polyorganosiloxanes employed in health care are especially suitable. In one aspect of the present disclosure, the polyorganosiloxane includes one or more polyorganosiloxanes composed principally of dimethylsiloxane units (e.g., dimethicone and/or a crosslinked dimethicone).

In the dispersions of the present disclosure, the encapsulated material is encapsulated by a polymeric membrane. The polymeric membrane, in turn, can be formed by coacervation, i.e. by precipitation of charged polymers with opposite charges. Within a coacervate, the bonds binding the charged polymers together are ionic and are generally stronger than bonds of the electrostatic present within a membrane of a surfactant.

In one aspect of the present disclosure, the polymeric membrane encapsulating the material, e.g. a polyorganosiloxane or an aqueous composition, can be formed by coacervation of at least two charged polymers with opposite polarities (or polyelectrolyte) and preferably in the presence of a first anionic polymer and a second cationic polymer, different from the first polymer.

Anionic polymers useful for forming the polymeric membrane encapsulating the one or more polyorganosiloxanes of the present disclosure include one or more polymers having anionic groups thereon. Such polymers may also be referred to as an anionic polyelectrolyte. By anionic group, is meant a chemical group, e.g., AH, which is capable of yielding a proton (H) to obtain the anion (A-). Depending on the conditions of the medium in which it is found, the anionic polymer therefore includes chemical functions in the AH form, or else in the form of its conjugate base A-. Exemplary anionic groups include carboxylic acid groups, e.g., —COOH, optionally present in the form of a carboxylate anion, e.g., —COO—. Anionic polymers suitable for the present disclosure include polymers formed by the polymerization of monomers, at least one portion of which bears an anionic group, such as carboxylic acid functions. Such monomers are for example acrylic acid, maleic acid or any ethylenically unsaturated monomer including at least one carboxylic acid function. Among the examples of anionic polymers, suitable for the present disclosure include linear or branched polymers or copolymers of acrylic acid or maleic acid and of other monomers, such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxypolyethyleneglycol methacrylates, hydroxyl ester acrylates. In one aspect of the present disclosure, the anionic polymer is a polyacrylic acid, e.g., carbomer.

Cationic polymers useful for forming the polymeric membrane encapsulating the one or more polyorganosiloxanes of present disclosure include polymers having cationic groups. Such polymers may also be referred to as a cationic polyelectrolyte. By cationic group, is meant a chemical group (e.g., B) capable of capturing a proton in order to obtain a BH+ group. Depending on the conditions of the medium in which it is found, the cationic polymers therefore include chemical functions in the B form, or else in the BH+ form, its conjugate acid. Examples of cationic groups include primary, secondary and tertiary amine groups, optionally present in the form of ammonium cations.

Example cationic polymers include polymers formed by the polymerization of monomers, at least one portion of which bearing a cationic group, such as primary, secondary or tertiary amine functions. Monomers having cationic groups include for example aziridine, or any ethylenically unsaturated monomer including at least one primary, secondary or tertiary amine function. Suitable cationic polymers include amodimethicone, derivatives of amodimethicone, such as for example copolymers of amodimethicone, aminopropyl dimethicone and more generally silicone polymers including amine functions. Additional cationic polymers include the copolymer of bis-isobutyl PEG-14/amodimethicone and bis-hydroxy/methoxy amodimethicone, polysaccharides comprising amine functions, such as chitosan or guar gum derivatives (guar hydroxypropyltrimonium chloride), polypeptides comprising amine functions such as polylysine, polyethyleneimines comprising amine functions such as linear or branched polyethyleneimine.

In one aspect of the present disclosure, one or more polyorganosiloxanes can be encapsulated by coacervation which generally involves combining a first formulation containing an anionic polymer in an aqueous medium and a second formulation containing the polyorganosiloxane and a cationic polymer. The anionic polymer and cationic polymer then form the polymeric membrane encapsulating the polyorganosiloxane dispersed in the aqueous medium. The formation of the polymeric membrane by these two polymers is generally caused by a modification of the conditions of the reaction medium (temperature, pH, concentration of reagents, etc.). The coacervation reaction results from the neutralization of these two charged polymers with opposite polarities and allows the formation of a membrane structure by electrostatic interactions between the first and the second polymer. The thereby formed membrane encapsulates the polyorganosiloxane and isolates it from an incompatible medium, e.g., an aqueous medium. The average size of the encapsulated hydrophilic aqueous composition is preferably less than about 500 μm, such as between 5 to 300 μm, e.g., between 10 to 100 μm.

Combining the first and second formulations to form the dispersion can be achieved by a microfluidic device, static mixer and/or dynamic mixer. Additional information about forming such coacervates can be found in WO 2012/120043, which is incorporated herein by reference.

In one aspect of the present disclosure, one or more polyorganosiloxanes, e.g., one or more polyorganosiloxanes composed principally of dimethylsiloxane units (dimethicone and/or a crosslinked dimethicone), is encapsulated by a polymeric membrane composed of a polyacrylic acid, e.g., carbomer, and an amine functionalized polyorganosiloxane (amine functionalized methicone or dimethicone, e.g., amodimethicone). The encapsulated polyorganosiloxane can be dispersed in an aqueous medium or gel. The percentage of the encapsulated polyorganosiloxane in the dispersion can vary. In one embodiment the percentage of the encapsulated polyorganosiloxane with or without additional ingredients and actives can be about from 1%-70% of the overall dispersion on a weight basis, e.g., from about 30%-50%, such as about 40%. The average size of the encapsulated aqueous composition is preferably less than about 500 μm. The amount of the cationic polymer comprising the encapsulated polyorganosiloxane can vary. In one aspect the amount of the cationic polymer comprising the encapsulated polyorganosiloxane is from about 0.01% to about 10% of the encapsulated polyorganosiloxane. The dispersions of the present disclosure can also be of relatively high viscosity, e.g., greater than about 20,000 cP, such as greater than about 30,000, 40,000 or greater than about 50,000 cP.

In an analogous manner, dispersions of an aqueous composition in a substantially immiscible polyorganosiloxane medium can be prepared. A polymeric membrane encapsulating the aqueous composition can be formed by coacervation of at least two charged polymers with opposite polarities (or polyelectrolyte) and preferably in the presence of a first anionic polymer and a second cationic polymer, different from the first polymer. The same cationic and anionic polymers described above for encapsulating one or more polyorganosiloxane in an aqueous medium can be used to encapsulate an aqueous composition in a polyorganosiloxane medium.

For example, an aqueous composition can be encapsulated by coacervation which generally involves combining a first formulation containing cationic polymer in a polyorganosiloxane medium and a second formulation containing the anionic polymer and aqueous composition. The cationic polymer and anionic polymer then form the polymeric membrane encapsulating the aqueous composition dispersed in the polyorganosiloxane medium. The formation of the polymeric membrane by these two polymers is generally caused by a modification of the conditions of the reaction medium (temperature, pH, concentration of reagents, etc.). The coacervation reaction results from the neutralization of these two charged polymers with opposite polarities and allows the formation of a membrane structure by electrostatic interactions between the first and the second polymer. The thereby formed membrane encapsulates the aqueous composition and isolates it from an incompatible polyorganosiloxane medium.

In one aspect of the present disclosure, an aqueous composition is encapsulated by a polymeric membrane composed of a polyacrylic acid, e.g., carbomer, and an amine functionalized polyorganosiloxane (amine functionalized methicone or dimethicone, e.g., amodimethicone). The encapsulated aqueous composition can be dispersed in a polyorganosiloxane medium, e.g., one or more polyorganosiloxanes composed principally of dimethylsiloxane units (dimethicone and/or a crosslinked dimethicone). The percentage of the encapsulated aqueous composition in the dispersion can vary. In one embodiment, the percentage of the encapsulated aqueous composition with or without additional ingredients and actives can be about from 1%-70% of the overall dispersion on a weight basis, e.g., from about 30%-50%, such as about 40%. The average size of the encapsulated aqueous composition is preferably less than about 500 μm. The amount of the anionic polymer comprising the encapsulated aqueous composition can vary. In one aspect the amount of the anionic polymer comprising the encapsulated aqueous composition is from about 0.01% to about 10% of the encapsulated material. The dispersions of the present disclosure can also be of relatively high viscosity, e.g., greater than about 20,000 cP, such as greater than about 30,000, 40,000 or greater than about 50,000 cP.

Dispersions comprising an encapsulated material by a polymeric membrane wherein the dispersion does not include a surfactant for dispersing the encapsulated material in the medium can include additional ingredients. The other ingredients can be encapsulated with the material by including the other ingredients in the formulation with the material to be encapsulated when forming the polymeric membrane encapsulating the material. Additional ingredients can also be included in the medium by incorporating the additional ingredients with the medium.

The dispersions of the present disclosure can be used as such or can be used to prepare other compositions, e.g. topical compositions that can be applied to human skin and/or hair. Such compositions are suitable for personal care and health care applications such as but not limited to serums, lotions, creams, pastes, liquid to powder, powders, cleansers and soaps, rinses, sprays, shampoos, conditioners, lacquers, balms, glosses, pomades, fixatives, dressings, lubricants, shaving aids and foams, dyes, bleaches, oils, gels, masks, patches.

There are several advantages of using the dispersions of the present disclosure in preparing topical compositions. For example, the dispersions of the present disclosure include ability to incorporate a substantially hydrophobic ingredient with the polyorganosiloxane and have that hydrophobic ingredient dispersed in an immiscible aqueous medium without the use of a surfactant. Topical skin compositions free of surfactants can be an advantage since surfactants can cause skin irritation.

The dispersions of the present disclosure can incorporate a cationic ingredient with the polyorganosiloxane, e.g., an amine functionalized polyorganosiloxane, and have that cationic ingredient dispersed in an immiscible aqueous medium without the use of a preservative. Topical skin compositions free of preservatives can be an advantage since preservatives can cause skin irritation.

In addition, dispersions of an aqueous composition in a polyorganosiloxane medium can result in dispersion having a smooth silicone feel followed by a fresh and light touch and finishing with a powdery veil. Such dispersions can be customized by encapsulating one or several water-soluble ingredients especially water-soluble actives into the internal phase to protect the ingredients and deliver it during the application on the skin. These dispersions can also be incorporated in an oil-in-water formulation or a water-in-oil formulation or an anhydrous formulation, such as an anhydrous facial serum or primer, to achieve both a light and powdery feel while delivering a water-soluble ingredient to the skin. Many actives in the beauty care market are water-based so dispersions of an aqueous composition in a polyorganosiloxane medium are particularly useful.

In addition, the dispersions of the present disclosure also allow forming a variety of topical composition that can have varied textures, appearance and sensory aspects that are not readily possible by incorporating a polyorganosiloxane directly into the same composition. The dispersions of the present disclosure more readily allow incorporating higher molecular weight or viscous hydrophobic material into a given aqueous medium The dispersions of the present disclosure also allow forming visually transparent or visually translucent topical compositions, such as cosmetics and sunscreens. Further advantages include increased homogeneity of the polyorganosiloxane film and thinner or thicker films with lighter or heavier skin feel may be produced without changing the texture of the composition. Other advantages include dosage and rate control of active agents for delivery.

Additional ingredients that can be included with encapsulated polyorganosiloxane include for example, one or more synthetic or natural oils. Oils useful for the present disclosure include: (i) organic compounds, (ii) compounds containing a silicon atom as enumerated above, (iii) mixtures of organic compounds, (iv) mixtures of compounds containing a silicon atom, or (v) mixtures of organic compounds and compounds containing a silicon atom.

The oil can serve to dissolve, suspend, or change the physical properties of other materials. Suitable oils include, but are not limited to, natural oils such as coconut oil; hydrocarbons such as mineral oil and hydrogenated polyisobutene; fatty alcohols such as octyldodecanol; esters such as $C_{12}$-$C_{15}$ alkyl benzoate; diesters such as propylene dipelargonate; and triesters, such as glyceryl trioctanoate. The organic oil components can also be mixtures of oils of differing viscosities. Examples of low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octyldodecanol, or mixtures of octyldodecanol, acetylated lanolin alcohol, cetyl acetate, isododecanol, polyglyceryl-3-diisostearate, or mixtures thereof. The high viscosity oils can include castor oil, lanolin and lanolin derivatives, triisocetyl citrate, sorbitan sesquioleate, $C_{10}$-$_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. Mention may be made, among the optional other non-silicone fatty substances, of mineral oils, such as liquid paraffin or liquid petroleum, of animal oils, such as perhydrosqualene or arara oil, or alternatively of vegetable oils, such as sweet almond, calophyllum, palm, castor, avocado, jojoba, olive or cereal germ oil. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols.

One or more active agents such as those for personal care, health care and/or pharmaceutically active agents can be included with the polyorganosiloxane. As used herein, a personal care active means any agents or mixtures of agents that are known in the art as additives in personal care compositions that are typically added for the purpose of treating hair or skin to provide a cosmetic, aesthetic, protective or sensory benefit. A healthcare active means any agent or mixtures of agents that are known in the art to provide a pharmaceutical or medical benefit. Thus, healthcare active include materials considered as an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Thus, active ingredient can include any agent that is intended to furnish pharmacological activity or other direct effect in the diagnosis, cure, mitigation, treatment, or prevention of disease, or to affect the structure or any function of the body of a human or other animals. The phrase can include those agents that may undergo chemical change in the manufacture of drug products and be present in drug products in a modified form intended to furnish the specified activity or effect. Some representative examples of active ingredients include; drugs, vitamins, minerals; hormones;

topical antimicrobial agents such as antibiotic active ingredients, antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients; active ingredients for the control of dandruff, seborrheic dermatitis, or psoriasis; and sunburn prevention and treatment agents.

Active agents can include vitamins and its derivatives, including "pro-vitamins". Vitamins useful herein include, but are not limited to, Vitamin $A_1$, retinol, $C_2$-$C_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin $B_1$, Vitamin $B_2$, Pro Vitamin B5, panthenol, Vitamin $B_6$, Vitamin $B_{12}$, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl)phosphate.

The active ingredient can be an active pharmaceutical ingredient. The active ingredient used in processes according to the invention can be a water-soluble or an oil-soluble active drug ingredient. Representative examples of some suitable water-soluble active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, and mebendazole. Representative examples of some suitable oil-soluble active drug ingredients which can be used are clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole, clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids. Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

The active can be a protein, such as an enzyme. Encapsulation benefits include segregation of the active agent against degradation by other ingredient in the formulation. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Said protease include, but are not limited to, trypsin, chymotrypsin, pepsin, pancreatin and other mammalian enzymes; papain, bromelain and other botanical enzymes; subtilisin, epidermin, nisin, naringinase (L-rhammnosidase) urokinase and other bacterial enzymes. Said lipase include, but are not limited to, triacyl-glycerol lipases, monoacyl-glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

The active agent can also be a sunscreen agent. The sunscreen agent can be selected from any sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)]Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer. These sunscreen agents can be selected one or combination of more than one. Alternatively, the sunscreen agent is a cinnamate based organic compound, or alternatively, the sunscreen agent is octyl methoxycinnamate, such as Parsol MCX or Uvinul® MC 80 an ester of para-methoxycinnamic acid and 2-ethylhexanol.

For certain applications, the composition can also contain a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentan one, 1-(p-Menthen-6(2)-yl)-1-propanone, 4-(4-Hydroxy-3-methoxyphenyl)-2-butanone, 2-Acetyl-3,3-Dimethyl-Norbomane, 6,7-Dihydro-1,1,2,3,3-Pentamethyl-4(5H)-Indanone, 4-Damascol, Dulcinyl or Cassione, Gelsone, Hexalon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran. Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethy]-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6))-decylidene-8)-butanal, octahydro-4,7-methano-1H-indenecarboxaldehyde, 3-ethoxy-4-hydroxy benzaldehyde, para-ethyl-alpha, alpha-di methyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carboxaldehyde, 5 or 6 methoxyl 0 Hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyloctanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof. Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethy]-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6))-decylidene-8)-butanal, octahydro-4,7-methano-1H-indenecarboxaldehyde, 3-ethoxy-4-hydroxy benzaldehyde, para-ethyl-alpha, alpha-di methyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carboxaldehyde, 5 or 6 methoxyl 0 Hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

A plant extract may also be added. Examples of these components are as follows: Ashitaba extract, avocado extract, *hydrangea* extract, Althea extract, *Arnica* extract, aloe extract, apricot extract, apricot kernel extract, *Ginkgo Biloba* extract, fennel extract, turmeric [*Curcuma*] extract, oolong tea extract, rose fruit extract, *Echinacea* extract, *Scutellaria* root extract, Phellodendro bark extract, Japanese *Coptis* extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, *Artemisia* extract, *Glycyrrhiza* extract, hibiscustea extract, *Pyracantha Fortuneana* Fruit extract, Kiwi extract, Cinchona extract, cucumber extract, guanocine, *Gardenia* extract, Sasa Albo-*marginata* extract, *Sophora* root extract, Walnut extract, Grapefruit extract, *Clematis* extract, *Chlorella* extract, mulberry extract, *Gentiana* extract, black tea extract, yeast extract, burdock extract, rice bran ferment extract, rice germ oil, comfrey extract, collagen, cowberry extract, *Gardenia* extract, *Asiasarum* Root extract, Family of *Bupleurum* extract, umbilical cord extract, *Salvia* extract, *Saponaria* extract, Bamboo extract, *Crataegus* fruit extract, *Zanthoxylum* fruit extract, shiitake extract, *Rehmannia* root extract, gromwell extract, *Perilla* extract, linden extract, *Filipendula* extract, peony extract, Calamus Root extract, white birch extract, Horsetail extract, *Hedera Helix* (Ivy) extract, hawthorn extract, *Sambucus nigra* extract, *Achillea millefolium* extract, *Mentha piperita* extract, sage extract, mallow extract, *Cnidium officinale* Root extract, Japanese green gentian extract, soybean extract, jujube extract, thyme extract, tea extract, clove extract, *Gramineae imperata* cyrillo extract, *Citrus unshiu* peel extract Japanese Angellica Root extract, *Calendula* extract, Peach Kernel extract, Bitter orange peel extract, Houttuyna *cordata* extract, tomato extract, natto extract, *Ginseng* extract, Green tea extract (*camellica sinesis*), grape seed extract, garlic extract, wild rose extract, *hibiscus* extract, *Ophiopogon* tuber extract, *Nelumbo nucifera* extract, parsley extract, honey, *hamamelis* extract, *Parietaria* extract, Isodonis herba extract, bisabolol extract, Loquat extract, coltsfoot extract, butterbur extract, Porid *cocos* wolf extract, extract of butcher's broom, grape extract, propolis extract, luffa extract, safflower extract, peppermint extract, linden tree extract, *Paeonia* extract, hop extract, pine tree extract, horse chestnut extract, Mizu-bashou (*Lysichiton camtschatcese*) extract, Mukurossi peel extract, Melissa extract, peach extract, cornflower extract, *eucalyptus* extract, saxifrage extract, citron extract, *coix* extract, mugwort extract, lavender extract, apple extract, lettuce extract, lemon extract, Chinese milk vetch extract, rose extract, rosemary extract, Roman Chamomile extract, and royal jelly extract.

Also flavoring agents can be added such as oil of wintergreen; peppermint oil; spearmint oil; menthol; vanilla; cinnamon oil; clove oil; bay oil; anise oil; *eucalyptus* oil; thyme oil; cedar leaf oil; oil of nutmeg; oil of sage; *cassia* oil; cocoa; licorice; high fructose corn syrup; *citrus* oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

Powders can be added for cosmetic or health effect to the dispersion or topical composition such as coloring agents such as pigments, dyes, inks or active agents which combine to produce color, powders to affect visual aspect or to prevent or treat the skin such as antifungal properties of ZnO. Typical pigments such as $TiO_2$, ZnO and treated pigments, pigment masterbatches or dispersions. Suitable face powders generally contain a dry particulate matter having a particle size of 0.02 to 200, preferably 0.5 to 100 microns. The particulate matter may be colored or non-colored (for example white). Suitable powders include bismuth oxychloride, titanated mica, fumed silica, spherical silica, polymethylmethacrylate, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarine and chromium or chromium hydroxide colors, and mixtures thereof.

The ability to include additional ingredients encapsulated with the polyorganosiloxane is advantageous in preparing other compositions, such as topical compositions. In one aspect of the present disclosure, a topical composition, e.g., a cosmetic or sunscreen, includes one or more polyorganosiloxane and optionally one or more additional ingredients encapsulated by a polymeric membrane. The encapsulated material is preferably dispersed in an aqueous medium or gel. Advantageously the topical composition is free of surfactants for dispersing the encapsulated material in the medium. The topical composition can also include other ingredients in the aqueous medium or encapsulated material such as synthetic, natural or modified oils, waxes, esters, fragrances, flavorings, plant extracts, vitamins, proteins and biologically derived agents, sunscreens, particulate powders and pigments, colors, dyes, personal care active agents, healthcare active agents and pharmaceutically active agents.

In one aspect of the present disclosure a topical composition comprises an encapsulated material dispersed in an aqueous medium wherein the encapsulated material includes one or more polyorganosiloxane and optionally one or more additional ingredients encapsulated by a polymeric membrane. The topical composition can be made visually transparent or visually translucent by matching the refractive index of the encapsulated material to the aqueous medium of the topical composition. In one embodiment, glycerin can be added to the aqueous medium to prepare such transparent or translucent topical compositions. Glycerin also advantageously has a synergetic effect with the encapsulated material in terms of texture.

Glycerin is a water-soluble and inexpensive ingredient, with humectant properties and with a high refractive index of 1.46. It is commonly used in beauty care products. However, the sensory feel of glycerin in such products is very sticky and, in particular, at high levels, e.g., where glycerin is included in the product at greater than 10% by weight. Glycerin can be used with the dispersions of the present disclosure to match the refractive index of the polyorganosiloxane, which typically have a refractive index of about 1.40, to obtain transparent formulation. In most of the cases, the quantity used to reach a visually transparent encapsulated polyorganosiloxane in aqueous medium is between 15 wt % to 65 wt % of glycerin in the overall formulation, e.g., between 20 wt % to 55 wt % or between 25 wt % to 50 wt % of glycerin in the overall formulation. However, even with such a large amount of glycerin in the aqueous medium, the sensory feel of certain dispersions and compositions of the present disclosure is not sticky at all. Hence, there appears to be a synergy between glycerin and an encapsulated polyorganosiloxane dispersion in terms of sensory feel. Advantageously, the dispersions of the present disclosure allow the use of a higher level of glycerin in the dispersion of composition containing the same and to obtain higher hydration without any appreciable sensation of tack.

In one aspect of the present disclosure, a topical composition comprises an encapsulated material dispersed in an aqueous medium wherein the encapsulated material includes one or more polyorganosiloxane and optionally one or more additional ingredients encapsulated by a polymeric membrane. The topical composition can include glycerin at higher than previously desired amounts while still exhibiting advantageous textural characteristics. These synergistic textural characteristics include reducing tack generally associated with high levels of Glycerin. The use of high levels of Glycerin imparts the ability to offer increased moisturization and hydration when applied topically

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Dispersions

Dispersions of encapsulated materials in media were prepared. The process included separately preparing an inner formulation (IF) and an outer formulation (OF). For preparing encapsulated polyorganosiloxanes, the IF included a cationic polymer, e.g., amodimethicone, and one or more polyorganosiloxanes. The OF included an anionic polymer, e.g., carbomer, in an aqueous medium. For preparing encapsulated aqueous compositions, the IF contained an anionic polymer e.g., carbomer, and the OF included a cationic polymer, e.g., amodimethicone, together with one or more polyorganosiloxanes.

Dispersions of the encapsulated material in the medium were prepared by combining the IF with the OF. When the polymers from the respective IF and OF come to the silicone/water interface they become both charged and attract each other. The coacervate newly created at the interface is partially soluble into each phase but not fully soluble in any. The polymeric membrane is then trapped at the interface. The polymeric membrane offers good protection against coalescence (fusion of droplets) and is self-healing. That means that if an encapsulate material is divided in several droplets, the membrane will be formed onto the new silicone/water interface (if there is enough polymer in each phase) to encapsulate the material. This self-healing capacity is used during the production of the following dispersions.

In addition, the viscosity of the OF (e.g., aqueous phase with carbomer) was controlled. The viscosity is a function of the type of carbomer, its concentration and also of the pH. As carbomer solutions are often fluid at low pH (<4.5) and viscous above pH 5, a third solution was used to control the viscosity during the process (named BASE in the example). This solution was made of water and base, e.g., sodium hydroxide.

The dispersions were produced from a coarse emulsion (droplets >500 μm) made by microfluidics or classical emulsification process from OF and IF solutions. Then the size of the droplets was homogenized by controlled fragmentation. The controlled fragmentation can be achieved by microfluidic device, static mixer, or dynamic mixer.

Addition of BASE solution can be achieve directly into the OF, or before controlled fragmentation or after controlled fragmentation, as a function of the droplets size desired and of the process used.

The following dispersions were prepared to form visually translucent or transparent materials by matching the refractive index of each phase (e.g., the IF containing silicone phase and the OF containing water phase). Glycerin was used to increase the refractive index of the aqueous phase. Depending on the type of polyorganosiloxane and cationic polymer used in the IF, the refractive index can be different so the amount of glycerin used in aqueous phase (e.g., the IF) needed to be adjusted.

Dispersion 1 (Silicone in Water)

The following formulations were separately prepared.

| IF | | | |
|---|---|---|---|
| Commercial Name | Supplier | INCI Name | % w/w |
| CXG-1104 | NUSIL | Dimethicone (and) Dimethicone/Vinyl Dimethicone Crosspolymer | 32.00 |
| CSF-3100 (5 cSt) | NUSIL | Dimethicone | 67.50 |
| CAS-3131 | NUSIL | Amodimethicone | 0.50 |
| Total | | | 100 |

OF

| Commercial Name | Supplier | INCI Name | % w/w |
|---|---|---|---|
| Water | / | Aqua | 48.7938 |
| Microcare PE | THOR | Phenoxyethanol | 1.4815 |
| Microcare PTG | THOR | Pentylenglycol | 3.7037 |
| Tego Carbomer 340FD | EVONIK | Carbomer | 0.4630 |
| Glycerine codex (99%) | INTERCHIMIE | Glycerin | 45.5000 |
| EDETA BD | BASF | Disodium EDTA | 0.0556 |
| Sodium Hydroxide Pellets PRS codex | PANREAC | Aqua; Sodium Hydroxyde | 0.0025 |
| Total | | | 100 |

BASE

| Commercial Name | Supplier | INCI Name | % w/w |
|---|---|---|---|
| Water | / | Aqua | 99.37725 |
| Sodium Hydroxide Pellets PRS codex | PANREAC | Aqua; Sodium Hydroxyde | 0.62275 |
| Total | | | 100 |

The IF contained several polyorganosiloxanes with amodimethicone as the cationic polymer. The OF contained carbomer as the anionic polymer, glycerin and several preservatives.

The IF was then added to the OF to form a biphasic mixture, which was quickly mixed with an overhead mixer in order to obtain a coarse dispersion. The coarse dispersion was then homogenized by injection through a static mixer to obtain a fine dispersion. The fine dispersion obtained was then gently mixed with the BASE solution in order to raise the pH and reach the final viscosity.

The ratio between the 3 solutions are shown in the following table:

| | % w/w |
|---|---|
| IF | 40.00% |
| OF | 54.00% |
| BASE | 6.00% |
| Total | 100% |

After this process, a translucent gel was obtained with the following composition:

Final Composition

| Commercial Name | Supplier | INCI Name | % w/w | % w/w PHASES |
|---|---|---|---|---|
| AQUEOUS PHASE | | | | |
| Water | / | Aqua | 32.312 | 53.857 |
| Microcare PE | THOR | Phenoxyethanol | 0.80 | 1.33 |
| Microcare PTG | THOR | Pentylenglycol | 2.00 | 3.33 |
| Tego Carbomer 340FD | EVONIK | Carbomer | 0.25 | 0.42 |
| Glycerine codex (99%) | INTER-CHIMIE | Glycerin | 24.57 | 40.95 |
| EDETA BD | BASF | Disodium EDTA | 0.03 | 0.05 |
| Sodium Hydroxide Pellets PRS codex | PANREAC | Aqua; Sodium Hydroxyde | 0.038 | 0.063 |
| Total | | | 60.00 | 100.00 |
| SILICONE PHASE | | | | |
| CXG-1104 | NUSIL | Dimethicone (and) Dimethicone/Vinyl Dimethicone Crosspolymer | 12.80 | 32.00 |
| CSF-3100 (5 cSt) | NUSIL | Dimethicone | 27.00 | 67.50 |
| CAS-3131 | NUSIL | Amodimethicone | 0.20 | 0.50 |
| Total | | | 40.00 | 100.00 |
| Total | | | 100.00 | |

Dispersion 2 (Silicone in Water)
The following formulations were separately prepared.

IF

| Commercial Name | Supplier | INCI Name | % w/w |
|---|---|---|---|
| CFF-3401 (1000 cPS) | NUSIL | Trifluoropropyl Dimethicone | 99.8000 |
| CAS-3131 | NUSIL | Amodimethicone | 0.2000 |
| Total | | | 100 |

OF

| Commercial Name | supplier | INCI Name | % w/w |
|---|---|---|---|
| Water | / | Aqua | 56.29595 |
| Microcare PE | THOR | Phenoxyethanol | 1.4815 |
| Microcare PTG | THOR | Pentylenglycol | 3.7037 |
| Tego Carbomer 340FD | EVONIK | Carbomer | 0.4630 |
| Glycerine codex (99%) | INTERCHIMIE | Glycerin | 38.0000 |
| EDETA BD | BASF | Disodium EDTA | 0.0556 |
| Sodium Hydroxide Pellets PRS codex | PANREAC | Aqua; Sodium Hydroxyde | 0.00025 |
| Total | | | 100 |

BASE

| Commercial Name | supplier | INCI Name | % w/w |
|---|---|---|---|
| Water | / | Aqua | 9937725 |
| Sodium Hydroxide Pellets PRS codex | PANREAC | Aqua; Sodium Hydroxyde | 0.62275 |
| Total | | | 100.00 |

The IF contained several polyorganosiloxanes with amodimethicone as the cationic polymer. The OF contained carbomer as the anionic polymer, glycerin and several preservatives.

The IF was then added to the OF to form a biphasic mixture, which was quickly mixed with an overhead mixer in order to obtain a coarse dispersion. The coarse dispersion was then homogenized by injection through a static mixer to obtain a fine dispersion. The fine dispersion obtained was then gently mixed with the BASE solution in order to raise the pH and reach the final viscosity.

The ratio between the 3 solutions are shown in the following table:

|  | % w/w |
|---|---|
| IF | 40.00% |
| OF | 54.00% |
| BASE | 6.00% |
| Total | 100% |

After this process a translucent gel was obtained with the following composition:

Final Composition

| Commercial Name | Supplier | INCI Name | % w/w | % w/w PHASES |
|---|---|---|---|---|
| AQUEOUS PHASE | | | | |
| Water | / | Aqua | 36.362 | 60.607 |
| Microcare PE | THOR | Phenoxyethanol | 0.80 | 1.33 |
| Microcare PTG | THOR | Pentylenglycol | 2.00 | 3.33 |
| Tego Carbomer 340FD | EVONIK | Carbomer | 0.25 | 0.42 |
| Glycerine codex (99%) | INTERCHIMIE | Glycerin | 20.52 | 34.20 |
| EDETA BD | BASF | Disodium EDTA | 0.03 | 0.05 |
| Sodium Hydroxide Pellets PRS codex | PANREAC | Aqua; Sodium Hydroxyde | 0.038 | 0.063 |
| Total | | | 60.00 | 100 |
| SILICONE PHASE | | | | |
| CFF-3401 (1000 cPS) | NUSIL | Trifluoropropyl Dimethicone | 39.92 | 99.80 |
| CAS-3131 | NUSIL | Amodimethicone | 0.08 | 0.20 |
| Total | | | 40.00 | 100 |
| Total | | | 100.00 | |

Dispersion 3 (Silicone in Water)
The following formulations were separately prepared.

IF

| Commercial Name | supplier | INCI Name | % w/w |
|---|---|---|---|
| CSF-3500 | NUSIL | Cyclopentasiloxane; Dimethicone | 12.5 |
| CSF-3100 (5 cSt) | NUSIL | Dimethicone | 87.3 |
| KF 8004 | SHIN ETSU | Amodimethicone | 0.2 |
| Total | | | 100 |

OF

| Commercial Name | supplier | INCI Name | % w/w |
|---|---|---|---|
| Water | / | Aqua | 50.641 |
| Microcare PE | THOR | Phenoxyethanol | 0.988 |
| Microcare PTG | THOR | Pentylenglycol | 2.469 |
| Tego Carbomer 340FD | EVONIK | Carbomer | 0.308 |
| Glycerine codex (99%) | INTERCHIMIE | Glycerin | 45.555 |
| EDETA BD | BASF | Disodium EDTA | 0.037 |
| Sodium Hydroxide Pellets PRS codex | PANREAC | Aqua; Sodium Hydroxyde | 0.00025 |
| Total | | | 100 |

BASE

| Commercial Name | supplier | INCI Name | % w/w |
|---|---|---|---|
| Water | / | Aqua | 99.578 |
| Sodium Hydroxide Pellets PRS codex | PANREAC | Aqua; Sodium Hydroxyde | 0.422 |
| Total | | | 100.00 |

The IF contained several polyorganosiloxanes with amodimethicone as the cationic polymer. The OF contained carbomer as the anionic polymer, glycerin and several preservatives.

The IF was then added to the OF to form a biphasic mixture, which was quickly mixed with an overhead mixer in order to obtain a coarse dispersion. The coarse dispersion was then homogenized by injection through a static mixer to obtain a fine dispersion. The fine dispersion obtained was then gently mixed with the BASE solution in order to raise the pH and reach the final viscosity.

The ratio between the 3 solutions are shown in the following table:

|  | % w/w |
|---|---|
| IF | 10.00% |
| OF | 81.00% |
| BASE | 9.00% |
| Total | 100% |

After this process a translucent gel was obtained with the following composition:

Final Composition

| Commercial Name | Supplier | INCI Name | % w/w | % w/w PHASES |
|---|---|---|---|---|
| AQUEOUS PHASE | | | | |
| Water | / | Aqua | 49.982 | 55.535 |
| Microcare PE | THOR | Phenoxyethanol | 0.8 | 0.889 |
| Microcare PTG | THOR | Pentylenglycol | 2 | 2.222 |
| Tego Carbomer 340FD | EVONIK | Carbomer | 0.25 | 0.278 |
| Glycerine codex (99%) | INTERCHIMIE | Glycerin | 36.9 | 41 |
| EDETA BD | BASF | Disodium EDTA | 0.03 | 0.033 |
| Sodium Hydroxide Pellets PRS codex | PANREAC | Aqua; Sodium Hydroxyde | 0.038 | 0.042 |
| Total | | | 90.00 | 100 |
| SILICONE PHASE | | | | |
| CSF-3500 | NUSIL | Cyclo-pentasiloxane; Dimethicone | 1.25 | 12.5 |
| CSF-3100 (5 cSt) | NUSIL | Dimethicone | 8.73 | 87.3 |
| KF 8004 | SHIN ETSU | Amodimethicone | 0.02 | 0.2 |
| Total | | | 10.00 | 100 |
| Total | | | 100.00 | |

Dispersion 4 (Silicone in Water)

The following formulations were separately prepared.

IF

| Commercial Name | supplier | INCI Name | % w/w |
|---|---|---|---|
| CFF-3401 (1000 cPS) | NUSIL | Trifluoropropyl Dimethicone | 99.8 |
| CAS-3131 | NUSIL | Amodimethicone | 0.2 |
| Total | | | 100 |

OF

| Commercial Name | supplier | INCI Name | % w/w |
|---|---|---|---|
| Water | / | Aqua | 59.531 |
| Microcare PE | THOR | Phenoxyethanol | 0.988 |
| Microcare PTG | THOR | Pentylenglycol | 2.469 |
| Tego Carbomer 340FD | EVONIK | Carbomer | 0.308 |
| Glycerine codex (99%) | INTERCHIMIE | Glycerin | 36.667 |
| EDETA BD | BASF | Disodium EDTA | 0.037 |
| Sodium Hydroxide Pellets PRS codex | PANREAC | Aqua; Sodium Hydroxyde | 0.00025 |
| Total | | | 100 |

BASE

| Commercial Name | supplier | INCI Name | % w/w |
|---|---|---|---|
| Water | / | Aqua | 99.578 |
| Sodium Hydroxide Pellets PRS codex | PANREAC | Aqua; Sodium Hydroxyde | 0.422 |
| Total | | | 100 |

The IF contained several polyorganosiloxanes with amodimethicone as the cationic polymer. The OF contained carbomer as the anionic polymer, glycerin and several preservatives.

The IF was then added to the OF to form a biphasic mixture, which was quickly mixed with an overhead mixer in order to obtain a coarse dispersion. The coarse dispersion was then homogenized by injection through a static mixer to obtain a fine dispersion. The fine dispersion obtained was then gently mixed with the BASE solution in order to raise the pH and reach the final viscosity.

The ratio between the 3 solutions are shown in the following table:

| | % w/w |
|---|---|
| IF | 10.00% |
| OF | 81.00% |
| BASE | 9.00% |
| Total | 100% |

After this process a translucent gel was obtained with the following composition:

Final Composition

| Commercial Name | Supplier | INCI Name | % w/w | % w/w PHASES |
|---|---|---|---|---|
| AQUEOUS PHASE | | | | |
| Water | / | Aqua | 57.182 | 63.536 |
| Microcare PE | THOR | Phenoxyethanol | 0.8 | 0.889 |
| Microcare PTG | THOR | Pentylenglycol | 2 | 2.222 |
| Tego Carbomer 340FD | EVONIK | Carbomer | 0.25 | 0.278 |
| Glycerine codex (99%) | INTERCHIMIE | Glycerin | 29.7 | 33 |
| EDETA BD | BASF | Disodium EDTA | 0.03 | 0.033 |
| Sodium Hydroxide Pellets PRS codex | PANREAC | Aqua; Sodium Hydroxyde | 0.038 | 0.042 |
| Total | | | 90.00 | 100 |
| SILICONE PHASE | | | | |
| CFF-3401 (1000 cPS) | NUSIL | Trifluoropropyl Dimethicone | 9.98 | 99.8 |
| CAS-3131 | NUSIL | Amodimethicone | 0.02 | 0.2 |
| Total | | | 10.00 | 100 |
| Total | | | 100.00 | |

Dispersion 5 (Water in Silicone)

The following formulations were separately prepared.

OF

| Commercial Name | Supplier | INCI Name | % w/w |
|---|---|---|---|
| CXG-1104 | NUSIL | Dimethicone (and) Dimethicone/Vinyl Dimethicone Crosspolymer | 45.0 |
| CSF-3100 (5 cSt) | NUSIL | Dimethicone | 54.8 |
| CAS-3131 | NUSIL | Amodimethicone | 0.2 |
| Total | | | |

IF

| Commercial Name | Supplier | INCI Name | % w/w |
|---|---|---|---|
| Water | / | Aqua | 53.87 |
| Microcare PE | THOR | Phenoxyethanol | 0.8 |
| Microcare PTG | THOR | Pentylenglycol | 2.0 |
| Carbopol ETD 2050 | LUBRIZOL | Carbomer | 0.2 |
| Glycerine codex (99%) | INTERCHIMIE | Glycerin | 43.0 |
| EDETA BD | BASF | Disodium EDTA | 0.03 |
| Sodium Hydroxide Pellets PRS codex | PANREAC | Aqua; Sodium Hydroxyde | 0.1 |
| Total | | | 100 |

The OF contained several polyorganosiloxanes with amodimethicone as the cationic polymer. The IF contained carbomer as the anionic polymer, glycerin and several preservatives.

The IF was then added to the OF to form a biphasic mixture, which was quickly mixed with an overhead mixer in order to obtain a coarse dispersion. The coarse dispersion was then homogenized by injection through a static mixer to obtain a fine dispersion.

The ratio between the 2 solutions are shown in the following table:

|  | % w/w |
|---|---|
| IF | 30% |
| OF | 70% |
| Total | 100% |

After this process, a translucent gel was obtained with the following composition:

Final Composition

| Commercial Name | Supplier | INCI Name | % w/w | % w/w PHASES |
|---|---|---|---|---|
| AQUEOUS PHASE | | | | |
| Water | / | Aqua | 16.19 | 53.96 |
| Microcare PE | THOR | Phenoxyethanol | 0.24 | 0.8 |
| Microcare PTG | THOR | Pentylenglycol | 0.6 | 2.0 |
| Carpopol ETF 2050 | Lubrizol | Carbomer | 0.06 | 0.2 |
| Glycerine codex (99%) | INTER-CHIMIE | Glycerin | 12.9 | 43 |
| EDETA BD | BASF | Disodium EDTA | 0.01 | 0.03 |
| Sodium Hydroxide Pellets PRS codex | PANREAC | Aqua; Sodium Hydroxyde | 0.003 | 0.01 |
| Total | | | 30.00 | 100.00 |
| SILICONE PHASE | | | | |
| CXG-1104 | NUSIL | Dimethicone (and) Dimethicone/Vinyl Dimethicone Crosspolymer | 31.5 | 45 |
| CSF-3100 (5 cSt) | NUSIL | Dimethicone | 38.36 | 54.8 |
| CAS-3131 | NUSIL | Amodimethicone | 0.14 | 0.2 |
| Total | | | 70.00 | 100.00 |
| Total | | | 100.00 | |

Topical Compositions

From Dispersions 1, 2, 3, 4 or 5, topical cosmetic compositions and topical sunscreen compositions were prepared.

Topical Composition 1: Anti-aging Day Cream

An oil in water topical composition for skin care was prepared using Dispersion 4 by a hot process wherein the composition contained encapsulated 3,3,3-trifluoropropyl-methldimethylpolysiloxanes. The following ingredients provided in the table below were used in the composition.

| A | Emulium Delta/Gattefossé | 4 | Cetyl Alcohol (and) Glyceryl Stearate (and) PEG-75 Stearate (and) Ceteth-20 (and) Steareth-20 |
|---|---|---|---|
| | Duraquench IQ/Croda | 2.5 | Cetyl Alcohol (and) Isostearyl Isostearate (and) Potassium Cetyl Phosphate (and) Cetyl Behenate (and) Behenic Acid |
| | Liponate NEB/Lipo Chemicals | 3 | C12-15 Alkyl Benzoate |
| | RevitElix/Croda | 3 | *Echium Plantagineum* Seed Oil |
| | Uvinul MC 80/BASF | 6.5 | Ethylhexyl Methoxycinnamate |
| | Neoheliopan 303/Symrise | 3 | Octocrylene |
| B | Dispersion 4 (CES 3401) @ 1,000 cP @ 10% | 40 | Pending |
| | Water | 30.1 | Water |
| C | Fleuri Frais/MNW | 0.1 | Perfume |

The process for preparing the topical composition included: (i) heating Phase A ingredients at 70° C. while gently mixing until completely melted, (ii) mixing Phase B ingredients until homogeneity and heat at 70° C., (iii) adding Phase B to Phase A and mixing with a rotor stator device. The mixture was maintained under agitation with medium shear until the dispersion was formed. Phase C was added to the mixture when T<40° C. and mixing was continued until the cream was homogeneous.

Topical Composition 2: Anti-aging Night Cream

A water in oil topical composition for skin care was prepared using Dispersion by a hot process, wherein the composition contain encapsulated 3,3,3-trifluoropropylm-ethyldimethyl-polysiloxanes. The following ingredients provided in the table below were used in the composition.

| Phase | Ingredient/Supplier | % | INCI |
|---|---|---|---|
| A | Water | 31 | Water |
| | Dispersion 4 (CES-3401) @ 1,000 cP @ 10% | 40 | Pending |
| | — | 2 | Propylene Glycol |
| B | Duraquench IQ/Croda | 5 | Cetyl Alcohol (and) Isostearyl Isostearate (and) Potassium Cetyl Phosphate (and) Cetyl Behenate (and) Behenic Acid |
| | Klearol/Sonneborn | 1 | Paraffinum Liquidum |
| | NaturaSoft Shea/Natura-Tec | 1 | Shea butter |
| | Crodacol C90/Croda | 1 | Cetyl Alcohol |
| | Neobee M5/Stepan | 3 | Caprylic/Capric Triglyceride |
| | Glucate SS/Lubrizol | 2.5 | Methyl Glucose Sesquistearate |
| | Glucamate SSE-20/Lubrizol | 0.5 | PEG-20 Methyl Glucose Sesquistearate |
| | Crodamol IPM/Croda | 8 | Isopropyl Myristate |
| C | Rose Noire/Luzi | 0.1 | Perfume |

The process for preparing the topical composition included: (i) heating Phase A ingredients at 70° C. while mixing, (ii) heating Phase B ingredients at 70° C. while gently mixing until completely melted, (iii) adding Phase A to Phase B while mixing with a rotor stator device. Mixing was continued with medium a shear device until the dispersion was formed. Phase C was added to the combined Phases AB when T<40° C. and mixed until the cream was homogeneous.

Topical Composition 3: Perfecting CC Cream

A water in silicone topical composition for color cosmetics was prepared using Dispersion 3 by a cold process wherein the composition contained encapsulated gum and low viscosity dimethylpolysiloxanes. The following ingredients provided in the table below were used in the composition.

| Phase | Ingredient/Supplier | % | INCI |
|---|---|---|---|
| A | CSS-7300/NuSil Technology | 3 | Cyclopentasiloxane (and) PEG/PPG-18/18 Dimethicone |
|  | Makibeads SP10/ Daito Kasei | 5 | Acrylates/Ethylhexyl Acrylate Crosspolymer |
|  | Daitopersion Ti-45/ Daito Kasei | 15 | Titanium Dioxide (and) Aluminium Hydroxide (and) Silica (and) Hydrogen Dimethicone (and) Lauryl PEG-9 Polydimethylsiloxyethyl Dimethicone (and) Dimethicone |
|  | Uvinul MC80/ BASF | 3 | Ethylhexyl Methoxycinnamate |
|  | Bentone 38V/ Elementis | 0.4 | Disteardimonium Hectorite |
| B | Dub ININ/ Stearinerie Dubois | 8 | Isononyl Isononanoate |
|  | OTS-5 Yellow no 5/ Daito Kasei | 0.04 | Triethoxycaprylylsilane (and) Yellow Iron Oxide |
|  | OTS-5 Blue no 1/ Daito Kasei | 0.01 | Triethoxycaprylylsilane (and) Blue Iron Oxide |
| C | Dispersion 3 (CES-3500) @ 10% | 55 | Pending |
|  | NaCl | 1 | Sodium Chloride |
|  | Trilon B/BASF | 0.05 | Tetrasodium EDTA |
|  |  | 0.1 | Perfume |
|  | Water | 6.4 | Water |
| D | Sugarcapsules Magic Brown | 3 | Mannitol (and) IRON OXIDES CI 77491, CI 77492 and CI 77499, Hydrogenated Lecithin (and) TiO2 (and) AlOH (and) Polymethyl Methacrylate |

The process for preparing the topical composition included: (i) premixing Phase B ingredients and then mixing Phase A and Phase B together with a medium shear device, (ii) premixing Phase C ingredients with a spatula until NaCl is dissolved, (iii) mixing Phase AB with a rotor stator and slowly adding Phase C to form the dispersion. Phase D ingredients were added directly into the dispersion and stir with a spatula very carefully to avoid breaking a significant amount of the capsules. Hydrolization of the capsules takes approximately 10 minutes after the final mix has been made.

Topical Compositions 4, 5, 6, 7: Moisturizing Hydrogel

Oil in water topical compositions were prepared using either Dispersion 1, 3 or 4 by a cold process. The following ingredients provided in the tables below were used in the compositions.

Topical Composition 4

| Phase | Ingredient/Supplier | % | INCI |
|---|---|---|---|
| A | Water | 37.8 | Water |
|  | — | 2 | Propylene Glycol |
|  | — | 8 | Alcohol Denat. |
|  | Dispersion 4 (CES-3401) @ 1,000 cP @ 10% | 40 | Pending |
| B | Dub ININ/ Stearinerie Dubois | 5 | Isononyl Isononanoate |
|  | Simulgel INS 100/ Seppic | 6 | Hydroxyethyl Acrylate/Sodium Acryloyldimethyl Taurate Copolymer (and) Isohexadecane (and) Polysorbate 60 |
|  | Neobee M5/Stepan | 1 | Caprylic/Capric Triglyceride |
| C | Fit & Healthy/Luzi | 0.1 | Perfume |
|  | FDC Blue no 1 | 0.1 | CI 42091 (0.1% sol.) |

Topical Composition 5

| Phase | Ingredient/Supplier | % | INCI |
|---|---|---|---|
| A | Water | 7.8 | Water |
|  | — | 2 | Propylene Glycol |
|  | — | 8 | Alcohol Denat. |
|  | Dispersion 3 (CES-3500) @ 10% | 70 | Pending |
| B | Dub ININ/ Stearinerie Dubois | 5 | Isononyl Isononanoate |
|  | Simulgel INS 100/ Seppic | 6 | Hydroxyethyl Acrylate/Sodium Acryloyldimethyl Taurate Copolymer (and) Isohexadecane (and) Polysorbate 60 |
|  | Neobee M5/Stepan | 1 | Caprylic/Capric Triglyceride |
| C | Fit & Healthy/Luzi | 0.1 | Perfume |
|  | FDC Blue no 1 | 0.1 | CI 42091 (0.1% sol.) |

Topical Composition 6

| Phase | Ingredient/Supplier | % | INCI |
|---|---|---|---|
| A | Water | 57.8 | Water |
|  | — | 2 | Propylene Glycol |
|  | — | 8 | Alcohol Denat. |
|  | Dispersion 4 (CES 3401) @ 1,000 cP @ 10% | 20 | Pending |
| B | Dub ININ/ Stearinerie Dubois | 5 | Isononyl Isononanoate |
|  | Simulgel INS 100/ Seppic | 6 | Hydroxyethyl Acrylate/Sodium Acryloyldimethyl Taurate Copolymer (and) Isohexadecane (and) Polysorbate 60 |
|  | Neobee M5/Stepan | 1 | Caprylic/Capric Triglyceride |
| C | Fit & Healthy/Luzi | 0.1 | Perfume |
|  | FDC Blue no 1 | 0.1 | CI 42091 (0.1% sol.) |

Topical Composition 7

| Phase | Ingredient/Supplier | % | INCI |
|---|---|---|---|
| A | Water | 36.2 | Water |
|  | — | 2 | Propylene Glycol |
|  | — | 8 | Alcohol Denat. |
|  | Dispersion 1 (CES 1104) @ 40% | 41.6 | Dimethicone (and) Aqua (and) Glycerin (and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
| B | Dub ININ/ Stearinerie Dubois | 5 | Isononyl Isononanoate |
|  | Simulgel INS 100/Seppic | 6 | Hydroxyethyl Acrylate/Sodium Acryloyldimethyl Taurate Copolymer (and) Isohexadecane (and) Polysorbate 60 |
|  | Neobee M5/Stepan | 1 | Caprylic/Capric Triglyceride |
| C | Fit & Healthy/Luzi | 0.1 | Perfume |
|  | FDC Blue no 1 | 0.1 | CI 42091 (0.1% sol.) |

The process for preparing the topical compositions of 4, 5, 6 and 7 were each performed essentially the same way. The process included: (i) mixing Phase A ingredients with medium shear device, (ii) mixing Phase B ingredients, (iii) adding Phase B to Phase A while mixing at 2000 rpm. Phase C ingredients were added to the combined Phase AB and mixing continued until the hydrogel was homogeneous.

Topical Composition 8: UV Protection Body Cream SPF 50

An oil in water topical composition for sun care was prepared using sunscreen actives and Dispersion 2 by a hot process wherein the composition contained encapsulated 3,3,3-trifluoropropylmethyldimethyl-polysiloxanes. The following ingredients provided in the table below were used in the composition.

| Phase | Ingredient/Supplier | % | INCI |
|---|---|---|---|
| A | Dispersion 2 (CES-3401) @ 1,000 cP @ 40% | 25 | Trifluoropropyl Dimethicone (and) Aqua (and) Glycerin (and) Pentylene Glycol (and) Phenoxyethanol (and) Carbomer (and) Amodimethicone (and) Sodium Hydroxide (and) Disodium EDTA |
|   | Water | 39.85 | Water |
|   | Trilon B/BASF | 0.05 | Tetrasodium EDTA |
| B | Uvinul MC80/BASF | 5 | Ethylhexyl Methoxycinnamate |
|   | Polycrylene/Hallstar | 5 | Polyester-8 |
|   | Solastay S1/Hallstar | 2 | Ethylhexyl Methoxycrylene |
|   | Hallbrite BHB/Hallstar | 5 | Butyloctyl Salicylate |
|   | Neoheliopan 357/Symrise | 3 | Avobenzone |
|   | Neoheliopan 303/Symrise | 8 | Octocrylene |
|   | Olivem 1000/Hallstar | 5 | Cetearyl Olivate (and) Sorbitan Olivate |
|   | Ecorol 68/50/Ecogreen | 2 | Cetearyl Alcohol |
| C | Crystals/IFF | 0.1 | Perfume |

The process for preparing the topical composition included: (i) mixing and heating Phase A ingredients to 80-85° C. while stirring continuously, (ii) heating Phase B ingredients to 80-85° C. and slowly adding Phase A under high shear (Ultra Turax/Silverson) to Phase A until homogeneous. After the mixture cooled to T<40° C., Phase C was added under medium shear. The pH was then adjusted to around 6 with sodium hydroxide.

Topical Composition 8: Snow White Primer

A water in oil topical compositions were prepared using Dispersion 5 by a cold process. The following ingredients provided in the tables below were used in the compositions.

| Phase | Ingredient/Supplier | % | INCI |
|---|---|---|---|
| A | Dispersion 5 (CEH-1104) @ 30% | 98 | Pending |
|   | Matlake OPA AS/Sensient | 1.5 | Titanium Dioxide/Alumina |
|   | Glamorous/International Flavors and Fragrances Inc. | 0.1 | Perfume |
|   | Sensaflash/Seppic | 0.2 | Glycerin (and) Acrylates Copolymer (and) VP/polycarbamyl Polyglycol Ester (and) Hydrolyzed Sesame Protein PG-propyl Methysilanediol |
|   | Sensiva PA 20/Schülke & Mayr | 0.2 | Phenethyl Alcohol (and) Ethylhexylglycerin |

The process for preparing the topical composition included mixing Phase A ingredients under high shear (Ultra Turax/Silverson) until the mixture becomes white, foamy, and homogenious.

Topical Composition 9:

A transparent, water-based serum was prepared by a cold process. The process included diluting Dispersion 1 (CES-1104 @ 40%) with a carbomer solution (Carbopol Ultrez 10 or Carbopol Ultrez 30 from Lubrizol). Moisturizing & anti-aging actives are added (Actiphyte of Cucumber from Active Organics and Hyaluronsäure 1% PHE from GfN). A perfume (Coconut & Vanilla Cream 933 from IFF) and glitters (MST-3 DK Pearl Gold from Daito Kasei) are added. The serum is mixed until homogeneity. Glycerin is added to adjust transparency.

Topical Composition 10:

A transparent, water-based serum was prepared by a cold process. The process included diluting Dispersion 2 (CES-3401@1,000 cP@40%) with a Sepimax Zen (aqueous polyacrylate) solution from Seppic. Moisturizing & anti-aging actives are added (Vivillume from Lonza and Black *Quinoa* from Crodarom). A perfume (Soft & Creamy 133 from IFF) and glitters (MST-3 DK Pearl Violet from Daito Kasei) are added. The serum is mixed until homogeneity. Glycerin was added to form a transparent composition.

Topical Composition 11: Anhydrous Foundation Mousse with CEH-1104

| Phase | Ingredient/Supplier | % | INCI |
|---|---|---|---|
| A | Dispersion 5 (CEH-1104) @ 30% | 54.6 | Pending |
|   | CPF-3300 @ 20 cP | 5 | Phenyl Trimethicone |
|   | Dub ININ | 10 | Isononyl Isononanoate |
| B | Uvinul MC80 | 2 | Ethylhexyl Methoxycinnamate |
|   | Daitopersion Zn-70-300 DM | 12 | Zinc Oxide (and) Dimethicone (and) PEG-10 Dimethicone (and) Hydrogen Dimethicone |
|   | FHS-3 Talc JA-46R | 8 | Talc/Perfluorooctyl Triethoxysilane |
|   | FHS-3 TiO2 CR-50 | 5 | Titane Dioxide/Aluminium Hydroxyde/Perfluorooctyl Triethoxysilane |
|   | FHS-3 Yellow LL100P | 1.32 | Iron Oxides Yellow/Perfluorooctyl Triethoxysilane |
|   | FHS-3 Red R-516P | 0.44 | Iron Oxides Red/Perfluorooctyl Triethoxysilane |
|   | FHS-3 Black BL-100P | 0.24 | Iron Oxides Black/Perfluorooctyl Triethoxysilane |
|   | — | 0.1 | Perfume |
|   | Paratexin NIB | 0.3 | Phenoxyethanol (and) Methylparaben (and) Butylparaben (and) Ethylparaben (and) Propylparaben |

A anhydrous mousse was prepared by cold process. The process for preparing the topical composition included mixing both Phase A and Phase B ingredients and adding phase B to Phase A while mixing.

Topical Composition 12: Pure Serum

An oil in water topical compositions were prepared using Dispersion 1 by a cold process. The following ingredients provided in the tables below were used in the compositions.

| Phase | Tradename | INCI | Supplier | % |
|---|---|---|---|---|
| A | Dispersion 1 (CES 1104) | Dimethicone (and) Aqua (and) Glycerin (and) Pentylene glycol (and) Dimethicone/Vinyl Dimethicone Crosspolymer (and) Amodimethicone (and) Carbomer (and) Phenoxyethanol (and) Sodium Hydroxide (and) Disodium EDTA | NuSil Technology | 11.3 |
|   | Carbopol Ultrez 30 | Carbomer | Lubrizol | 0.2 |
|   | Water | Water | — | 44.8 |
|   | Glycerin | Glycerin | — | 43.5 |
|   | NaOH | Sodium Hydroxide | — | q.s |

The process for preparing the topical composition include preparing an aqueous medium including the carbomer, water, glycerin and NaOH by slowing adding the cabomer into water with slow mixing followed by the other components of the aqueous medium with mixing. Dispersion 1 was then added to the formulation and mixed slowly until homogeneous. Air bubbles were removed with a vacuum bell when the solution was in a liquid state. The sodium hydrozide was added with medium mixing until the desired viscosity and pH were reached.

The moisturization property of Topical Composition 12 (Pure Serum) was tested by corneometry and compared to a commercial benchmark (NutriExtra Body Vichy) which claims 48 h hydration. Test was performed with Corneometer CM825® (COURAGE & KHAZAKA) on 11 panelists. Measurements were taken on treated and untreated area (forearms) at t=0. Then a standard quantity (2 µL/cm2) of NutriExtra or Pure Serum product was applied on panelists randomly and measurements were taken at t=0, t=24 h, t=48 h and t=72 h. The following data was obtained.

| | Products | Average Variation (UA) | Average Variation (%) | p Value for the comparison (Student test) | Significance |
|---|---|---|---|---|---|
| T = 24 h | NutriExtra Body Vichy | 4.9 | 22.2 | 0.5082 | Not significant |
| | Pure Serum | 5.7 | 25.4 | | (p > 0.05) |
| T = 48 h | NutriExtra Body Vichy | 3.3 | 14.2 | 0.9085 | Not significant |
| | Pure Serum | 3.2 | 15.1 | | (p > 0.05) |
| T = 72 h | NutriExtra Body Vichy | 1.7 | 8.2 | 0.5823 | Not significant |
| | Pure Serum | 2.1 | 10.6 | | (p > 0.05) |

The data in the table above shows that after 1 single application both products result in moisturization until 72 h. An emulsion is known to provide more moisturization than a water-based product because the oil phase coming from the emulsion acts as a film to form a semi-occlusive barrier on the skin to keep the moisture inside the skin. However, the water based Pure Serum composition provided statistically the same moisturization over time compared to an oil based emulsion NutriExtra even though Pure Serum contains a slight amount of oil (4% provided by the Dispersion 1 (CES 1104) as compared to about 30-35% contained in NutriExtra. Use of Dispersion 1 in the Pure Serum composition allows a high level of glycerin (about 43.5 wt %) to obtain higher hydration without any appreciable tack senation.

Topical Composition 13: Pure Mist

An oil in water topical compositions were prepared using Dispersion 1 by a cold process. The following ingredients provided in the tables below were used in the compositions.

| Phase | Ingredient/Supplier | % | INCI |
|---|---|---|---|
| A | Water | 39.32 | Water |
| | Carbopol Ultrez 30/Lubrizol | 0.05 | Carbomer |
| | TEA 90%/BASF | 0.03 | Triethylamine |
| B | Dispersion 1 (CES 1104) @ 40% | 8.4 | Dimethicone (and) Aqua (and) Glycerin (and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
| | Glycerin/INTERCHIMIE | 41 | Glycerin |
| | Ethanol | 11.2 | Alcohol Denatured |

The process for preparing the topical composition included mixing Phase B ingredients and slowly adding Phase B to Phase A until homogenous.

Topical Composition 14: Kiwi Exfoliating Gel

An oil in water topical compositions were prepared using Dispersion 1 by a cold process. The following ingredients provided in the tables below were used in the compositions.

| Phase | Ingredient/Supplier | % | INCI |
|---|---|---|---|
| A | Water | 46.66 | Water |
| | Glycerin/INTERCHIMIE | 42.5 | Glycerin |
| | Makimousse 400/Daito Kasei | 0.3 | Sodium Polyacrylate Starch |
| B | Dispersion 1 (CES 1104) @ 40% | 8.8 | Dimethicone (and) Aqua (and) Glycerin (and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
| | Cellulobeads D200/Daito Kasei | 0.9 | Cellulose |
| | Original Kiwi Extract/Gattefosse | 0.4 | *Actinidia Chinensis* (Kiwi) Fruit Extract |
| | FDC Yellow | 0.1 | — |
| | FDC Blue | 0.02 | — |
| | Kiwi Seeds and Melon/IFFF | 0.02 | — |
| C | Coconut Exfoliating Powder/Pacifique Sud | 0.3 | *Cocos Nucifera* (Coconut) Shell Powder |

The process for preparing the topical composition included mixing Phase A and Phase B ingredients independently. Phase A is added to Phase B while mixing. Phase C ingredients are slowly added until homogenous.

Topical Composition 15: Frosted Eye Cream

An oil in water topical compositions were prepared using Dispersion 1 by a cold process. The following ingredients provided in the tables below were used in the compositions.

| Phase | Ingredient/Supplier | % | INCI |
|---|---|---|---|
| A | Water | 74.7 | Water |
| | Simulgel INS 100/Seppic | 0.5 | Hydroxyethyl Acrylate/Sodium Acryloyldimethyl Taurate Copolymer (and) Isohexadecane (and) Polysorbate 60 |
| | Sepigel 305/Seppic | 1 | Polyacrylamide (and) C13-14 Isoparaffin (and) Laureth-7 |
| B | Dispersion 1 (CES 1104) @ 40% | 15 | Dimethicone (and) Aqua (and) Glycerin (and) Pentylene Glycol (and) Dimethicone/Vinyl Dimethicone Crosspolymer (and) Phenoxyethanol (and) Carbomer (and) |

-continued

| Phase | Ingredient/ Supplier | % | INCI |
|---|---|---|---|
| C | Aquakeep/ Sumitomo Seika | 0.5 | Amodimethicone (and) Sodium Hydroxide (and) Disodium EDTA Sodium Polyacrylate |
|  | Glycerin/ Interchemie | 5 | Glycerin |
| D | Sesaflash/Seppic | 2 | Glycerin & Acrylates Copolymer (and) VP/polycarbamy Polyglycol Ester (and) Hydrolyzed Sesame Protein PG-propyl Methylsilanediol |
|  | Adipoless/Seppic | 0.5 | Butylene Glycol (and) *Chenopodium Quinoa* Seed Extract |
|  | Euxyl PE 90/ Schülke & Mayr | 0.8 | Phenoxyethanol (and) Ethylhexylglycerin |

The process for preparing the topical composition included premixing Phase A, Phase C and Phase D, and slowly adding Phase B to Phase A until a white cream is obtained. Phase C is added to the mixture and stirred until a frosted aspect is obtained. Phase D is then added to the mixture until homogenous.

Topical Composition 16: Gelée de Teint

An oil in water topical compositions were prepared using Dispersion 1 and Dispersion 2 by a cold process. The following ingredients provided in the tables below were used in the compositions.

| Phase | Ingredient/ Supplier | % | INCI |
|---|---|---|---|
| A | Water | 60.19 | Water |
|  | SepiMax Zen | 1 | Polyacrylate Crosspolymer-6 |
| B | Dispersion 1 (CES 1104) @ 40% | 10 | Dimethicone (and) Aqua (and) Glycerin (and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
|  | Dispersion 2 (CES-3401) @ 1,000 cP @ 40% |  | Trifluoropropyl Dimethicone (and) Aqua (and) Glycerin (and) Pentylene Glycol(and) Phenoxyethanol (and) Carbomer (and) Amodimethicone (and) Sodium Hydroxide (and) Disodium EDTA |
| C | PEG-12 Dimethicone TiO2/Daïto Kasei | 9 | Titanium Dioxide (and) Silica (and) Aluminum Hydroxide |
|  | PEG-12 Dimethicone Yellow/ Daïto Kasei | 1.98 | Iron Oxides Yellow (and) Silica |
|  | PEG-12 Dimethicone Red/Daïto Kasei | 0.66 | Iron Oxides Red (and) Silica |
|  | PEG-12 Dimethicone Black/Daïto Kasei | 0.36 | Iron Oxides Black (and) Silica |
|  | MSS-500W/Kobo | 6 | Silica |
| D | Glamorous/IFF | 0.01 | Perfume |
|  | Euxyl PE 90/ Schülke & Mayr | 0.8 | Phenoxyethanol (and) Ethylhexylglycerin |

The process for preparing the topical composition included premixing Phase A and Phase C. Phase B ingredients are added to Phase A while mixing. Phase C ingredients are added to the mixture until homogenous. Phase D ingredients are then added to the mixture.

Topical Composition 17: Pure Mousse

A water in oil topical compositions were prepared using Dispersion 1 by a cold process. The following ingredients provided in the tables below were used in the compositions.

| Phase | Ingredient/ Supplier | % | INCI |
|---|---|---|---|
| A | Dispersion 1 (CES 1104) @ 40% | 15 | Dimethicone (and) Aqua (and) Glycerin (and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
|  | CPF-3300/Nusil Technologies | 10 | Phenyl Trimethicone |
|  | Dub-ININ/ Stearinerie Dubois | 9.5 | Isononyl Isononanoate |
|  | Bentone 38V/Elementis | 0.4 | Disteardimonium Hectorite |
|  | CSS-7302/Nusil Technology | 3 | PEG-10 Dimethicone |
|  | Univul MC 80/BASF | 2 | — |
|  | Daitospersion Ti-45 (DM)/ Daïto Kasei | 12 | Titanium Dioxide (and) Aluminium Hydroxide (and) Silica (and) Hydrogen Dimethicone (and) Lauryl PEG-9 Polydimethylsiloxyethyl Dimethicone (and) Dimethicone |
|  | FHS-3 Talc JA-46R/Daïto Kasei | 5 | Talc/Perfluorooctyl Triethoxysilane |
|  | Covabead Velvet 20/Sensient | 4 | Polymethyl Methacrylate |
| B | Water | 27.15 | Water |
|  | Triton B/BASF | 0.5 | Tetrasodium EDTA |
|  | Paratexin NIB/Azelis UK | 0.3 | Phenoxyethanol (and) Methylparaben (and) Butylparaben (and) Ethylparaben (and) Propylparaben |
|  | Summer Dreams/ IFF | 0.1 | Perfume |
| C | Dispersion 1 (CES 1104) @ 40% | 15 | Dimethicone (and) Aqua (and) Glycerin (and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
| D | Aerosil 200/ Evonik | 1.5 | Silica |

The process for preparing the topical composition included premixing Phase A and Phase B. Phase B ingredients are slowly added to Phase A while mixing. Phase C ingredients are added to the mixture until homogenous. Phase D ingredients are then added to the mixture until homogenous.

Topical Composition 18: Aerosol Mousse

An oil in water topical compositions were prepared using Dispersion 1 by a cold process. The following ingredients provided in the tables below were used in the compositions.

| Phase | Ingredient/Supplier | % | INCI |
|---|---|---|---|
| A | Water | 14.9 | Water |
|  | Phosphomer Cello PC 40KC/KCI | 0.35 | Hydroxyethylcellulose (and) Polyphosphorylcholine Glycol Acrylate |
| B | Dispersion 1 (CES 1104) @ 40% | 5.25 | Dimethicone (and) Aqua (and) Glycerin (and) Pentylene Glycol (and) Dimethicone/Vinyl Dimethicone Crosspolymer (and) Phenoxyethanol (and) Carbomer |

| Phase | Ingredient/Supplier | % | INCI |
|---|---|---|---|
| | | | (and) Amodimethicone (and) Sodium Hydroxide (and) Disodium EDTA |
| C | Nikkol PCB-44/Nikkol Chemicals | 0.25 | PPG-8 Ceteth-20 |
| | Intenste Moisture/IFF | 0.35 | Perfume |
| | Ethanol | 8.75 | Alcohol Denatured |
| | Monopropylene Glycol | 1 | Propylene Glycol |
| | Glycerin/Intercheme | 1 | Glycerin |
| | D-Panthenol 75W/Xinfu | 0.7 | Panthenol (and) Water |
| D | Clairezome AI/Regeron | 0.7 | Sh-Polypeptide-40 (and) Lecithin (and) Sodium Chloride (and) Sodium Phosphate (and) Disodium EDTA |
| | Actiphyte Calendula GL 100 NP/Active Organics | 0.7 | Glycerin (and) Calendula Officinalis Flower Extract |
| | Actiphyte of Chamomille GL100 NP/Active Organics | 0.7 | Glycerin (and) Chamomilla Recutita (Matricaria) Flower Extract |
| | Paratexin NIB/Azelis UK | 0.35 | Phenoxyethanol (and) Methylparaben (and) Butylparaben (and) Ethylparaben (and) Propylparaben |
| E | Nocaspray n-Butane 1,2 bar/Inventec | 65 | Butane |

The process for preparing the topical composition included premixing Phase A and Phase C. Phase B is added to Phase A while mixing. Phase C is then added to the mixture until homogenous. Phase D is then added to the mixture until homogenous. The mixture is then injected to an aerosol container and Phase E is injected, whereby the container is isolated.

Topical Composition 19: Twinkling Spray

An oil in water topical compositions were prepared using Dispersion 1 by a cold process. The following ingredients provided in the tables below were used in the compositions.

| Phase | Ingredient/Supplier | % | INCI |
|---|---|---|---|
| A | Water | 67.52 | Water |
| | Phosphomer CEM 510 KC/KCI | 0.1 | Acrylic Acid/Phosphorylcholine Glycol Acrylate Crosspolymer |
| B | TEA 90%/BASF | 0.05 | Triethylamine |
| B | Dispersion 1 (CES 1104) @ 40% | 5.25 | Dimethicone (and) Aqua (and) Glycerin(and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
| C | Ethanol | 8 | Acohol Denatured |
| | Glycerin/Intercheme | 5 | Glycerin |
| | Paratexin NIB/Azelis UK | 1 | Phenoxyethanol (and) Methylparaben (and) Butylparaben (and) Ethylparaben (and) Propylparaben |
| | Floral Explosion/IFF | 1 | Perfume |
| | Actiphyte Sacred Lotus GL 100 NP/Active Organics | 2 | Glycerin (and) Nelumbo Nucifera Flower Extract |
| | Candurin Light Gold/Merk | 0.15 | — |
| | Ronastar Golden Jewel/Merk | 0.18 | Calcium Aluminum Borosilicate (and) Titanium Dioxide (and) Silica (and) Iron Oxides (and) Tin Oxide |

The process for preparing the topical composition included premixing Phase A. Phase B is mixed into Phase A until homogenous. Phase C is added to the mixture until homogenous.

Topical Composition 20: Liquid Aqueous Lipstick

An oil in water topical compositions were prepared using Dispersion 1 by a cold process. The following ingredients provided in the tables below were used in the compositions.

| Phase | Ingredient/Supplier | % | INCI |
|---|---|---|---|
| A | Water | 54 | Water |
| | Dispersion 1 (CES 1104) @ 40% | 5.25 | Dimethicone (and) Aqua (and) Glycerin (and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
| | Paratexin NIB/Azelis UK | 0.4 | Phenoxyethanol (and) Methylparaben (and) Butylparaben (and) Ethylparaben (and) Propylparaben |
| B | Eutanol G | 17 | Octyldodecanol |
| | Bentone 38V/Elementis | 0.4 | Disteardimonium Hectorited |
| | Versagel ME 750/Calumet | 9 | Hydrogenated Polyisobutene (and) Ethylene/Propylene/Styrene Copolymer (and) Butylene/Ethylene/Styrene Copolymer |
| | Sepigel 305/Seppic | 3.7 | Plyacrylamide (and) C13-14 Isoparaffin (and) Laureth-7 |
| | CSV-3000/Nusil Technology | 15 | Cyclopentasiloxane |
| | Unipure Red LC 3075 ADT-C/Sensient | 0.5 | CI 15850 (and) Isopropyl Titanium Triisostearate (and) Bis-Hydroxyethoxypropyl Dimethicone (and) PEG-2 Soyamine (and) Isophorone Diisocyanate |

The process for preparing the topical composition included premixing Phase A and Phase B. Phase B is added to Phase A until homogenous.

Topical Composition 21: Powder to Cream Formulation

An oil in water topical compositions were prepared using Dispersion 1 by a cold process. The following ingredients provided in the tables below were used in the compositions.

| Phase | Ingredient/Supplier | % | INCI |
|---|---|---|---|
| A | Alumina AS-EM/Sensient | 5 | Alumina (and) Triethoxycaprylylsilane |
| | Talc AS R0435/Sensient | 9 | Talc (and) Triethoxycaprylyl Silane |
| | Covapearl Pink 433 | 2 | CI 77891 (and) Mica (and) |

-continued

| Phase | Ingredient/Supplier | % | INCI |
|---|---|---|---|
| | AS/Sensient | | Triethoxycaprylylsilane |
| | Covabead LH 70-3/Sensient | 2 | Methylmethacrylate Crosspolymer (and) Triethoxycaprylylsilane |
| B | Water | 63.95 | Water |
| | Dispersion 1 (CES 1104) @ 40% | 15 | Dimethicone (and) Aqua (and) Glycerin (and) Pentylene Glycol (and) Dimethicone/Vinyl Dimethicone Crosspolymer (and) Phenoxyethanol (and) Carbomer (and) Amodimethicone (and) Sodium Hydroxide (and) Disodium EDTA |
| | Summer Dreams/IFF | 0.05 | Perfume |
| | Covagel/Sensient | 3 | Sodium Carboxymethyl Starch |

The process for preparing the topical composition included blending Phase A in a mill, then adding Phase A to Phase B while stirring until homogenous.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A dispersion comprising an encapsulated material dispersed in a medium that is substantially immiscible with the encapsulated material, wherein the encapsulated material is encapsulated by a polymeric membrane, wherein the dispersion does not include a surfactant for dispersing the encapsulated material in the medium, wherein either the encapsulated material is an aqueous composition or the medium is an aqueous medium and glycerin is included in the aqueous composition or the aqueous medium in an amount greater than 10 wt % of the dispersion and wherein the average size of the encapsulated material dispersed in the medium is less than 500 microns.

2. The dispersion of claim 1, wherein the encapsulated material includes a polyorganosiloxane and the medium is the aqueous medium.

3. The dispersion of claim 1, wherein the polymeric membrane encapsulating the material is composed of a polyacrylic acid and an amine functionalized polyorganosiloxane.

4. The dispersion of claim 1, wherein the encapsulated material is the aqueous composition and the medium includes a polyorganosiloxane.

5. The dispersion of claim 1, wherein the dispersion includes glycerin in the aqueous composition or the aqueous medium in an amount between 15 wt % to 65wt %.

6. The dispersion of claim 1, wherein the dispersion is visually transparent.

7. The dispersion of claim 1, wherein the dispersion has a viscosity of greater than 20,000 cP.

8. A topical composition comprising the dispersion of claim 1.

9. The topical composition of claim 8, wherein the composition is a cosmetic.

10. The topical composition of claim 8, wherein the composition is transparent.

11. The topical composition of claim 8, wherein the composition is a transparent cosmetic and the medium is the aqueous medium and the composition further comprises glycerin.

12. The topical composition of claim 8, wherein the composition is a sunscreen.

13. The topical composition of claim 8, wherein the composition is a transparent or translucent sunscreen and the medium is the aqueous medium including glycerin.

14. The dispersion of claim 1, wherein the average size of the encapsulated material dispersed in the medium is between 5 microns to 300 microns.

15. A dispersion comprising an encapsulated polyorganosiloxane dispersed in an aqueous medium that is substantially immiscible with the encapsulated polyorganosiloxane, wherein the encapsulated polyorganosiloxane is encapsulated by a polymeric membrane, wherein the aqueous medium includes glycerin and wherein the average size of the encapsulated polyorganosiloxane dispersed in the aqueous medium is between 5 microns to 300 microns.

16. A dispersion comprising an encapsulated polyorganosiloxane dispersed in an aqueous medium that is substantially immiscible with the encapsulated polyorganosiloxane, wherein the encapsulated polyorganosiloxane is encapsulated by a polymeric membrane, wherein the aqueous medium includes glycerin in an amount greater than 10 wt % of the dispersion and wherein the average size of the encapsulated polyorganosiloxane dispersed in the aqueous medium is less than 500 microns.

* * * * *